United States Patent [19]

Kampf et al.

[11] 4,454,939
[45] Jun. 19, 1984

[54] APPARATUS FOR TRANSPORTING SAMPLE HOLDERS

[75] Inventors: Richard S. Kampf, Costa Mesa; Chul H. Sohn, Irvine; Aurangzeb K. Khan, Costa Mesa, all of Calif.

[73] Assignee: Beckman Instruments, Inc., Fullerton, Calif.

[21] Appl. No.: 330,933

[22] Filed: Dec. 15, 1981

[51] Int. Cl.³ ............................................. B65G 43/00
[52] U.S. Cl. .................................. 198/341; 198/472; 198/465; 250/328
[58] Field of Search ............... 198/339, 341, 345, 472, 198/580, 795, 465, 468, 572, 573; 141/130; 250/328

[56] References Cited

U.S. PATENT DOCUMENTS

| | | | |
|---|---|---|---|
| 3,221,781 | 12/1965 | Forsstrom | 141/130 |
| 3,236,321 | 2/1966 | Katagiri et al. | 177/114 |
| 3,544,272 | 12/1970 | Vaills | 23/253 |
| 3,552,536 | 1/1971 | Emary | 198/19 |
| 3,859,528 | 3/1973 | Luitwieler, Jr. et al. | 250/328 |
| 3,897,216 | 7/1975 | Jones | 141/130 |
| 4,029,961 | 6/1977 | Lohr et al. | 250/328 |
| 4,040,533 | 8/1977 | De Boer et al. | 198/472 |
| 4,147,250 | 4/1979 | Schulz | 198/472 |

FOREIGN PATENT DOCUMENTS 2277013 1/1976 France .
2331785 6/1977 France .

Primary Examiner—Joseph E. Valenza
Assistant Examiner—Daniel Alexander
Attorney, Agent, or Firm—R. J. Steinmeyer; R. R. Meads; A. A. Canzoneri

[57] ABSTRACT

Apparatus for transporting elongated sample holders in a sample holder storage compartment past an operating station at which sample tubes contained in the sample holders may be removed and then returned to the sample holders. First and second parallel conveyors on opposite sides of the operating station drive the holders toward and away from the operating station. Lateral drive means engage the holders in longitudinal stop positions at opposite ends of the conveyors and drive them laterally between the conveyors to lateral stop positions, one of the holders during lateral movement being driven into and away from an operative position at the operating station. Encoded label means are displayed on each sample holder for indicating the incremental spacing between the sample tubes carried in the sample holder. Detector means are provided for reading the encoded label means and convey a signal in accordance with the label means to control means which control the operation of the first and second conveyor means and of the lateral drive means.

6 Claims, 9 Drawing Figures 4,454,939

APPARATUS FOR TRANSPORTING SAMPLE HOLDERS

BACKGROUND OF THE INVENTION

The present invention relates to sample transport apparatus and, more particularly, to apparatus for circulating sample holders in a storage compartment past an operating station.

A prior art sample transport apparatus was disclosed in U.S. Pat. No. 3,859,528 issued to Luitwieler Jr. et al., issued Jan. 7, 1975 and assigned to Beckman Instruments, Inc., the assignee of the present invention. The prior art apparatus is designed for circulating a plurality of sample holder vials past an operating station. The vials are supported within holding trays which are circulated in rectilinear fashion in the sample storage compartment of the apparatus.

An elevator is provided at the operating station for removing a vial from the sample tray and positioning it in a radiation detection chamber for analysis, and then returning the vial to the sample tray in the compartment. A plurality of sample trays are contained in the storage compartment and grouped in two longitudinally extending, generally parallel columns on opposite sides of the operating station. Longitudinally movable fingers at opposite ends of each column move the entire column of trays incrementally, in a longitudinal direction, a distance of one tray depth to drive trays in the first column toward the operating station and trays in the second column away from the operating station. After moving each column of trays longitudinally, trays at the remote ends of the columns are indexed laterally from one column to the other after which the fingers again move the columns in increments of one tray depth.

Although the foregoing apparatus adequately performs its intended function, it does not possess certain advantages for which there is currently a demand. For example, as a result of the limited longitudinal drive capabilities of the incrementing fingers, incremental movement of each tray column requires that each tray abut an adjoining tray so that the trays can push each other serially in domino fashion.

The consequence of this arragement is that unless the apparatus contains a full load of trays, the incrementing finers will be unable to move the tray columns longitudinally to positions whereby the trays at the remote ends of the columns can be laterally indexed between columns. Also, when indexing, the apparatus may fail to accurately align a tray in position over the elevator at the operating station. In such a case, instead of engaging and removing the sample vial, the elevator will instead strike the tray and may jam the apparatus. In addition, there is no provision in the prior apparatus for detecting and correcting malfunctions of this kind.

There is, accordingly, need for sample transport apparatus having broader capabilities than those of the prior art. There is, for example, a need for apparatus which is capable of circulating sample holders of any number ranging from one to a full load and whereby a plurality of sample holder types, each adapted for carrying sample tubes of differing size and number can be freely mixed; and whereby jam-ups or stoppages of the transport apparatus are automatically detected and corrected.

SUMMARY OF THE INVENTION

The present invention provides apparatus for transporting elongated sample holders past an operating station in a sample holder storage compartment. Each sample holder is adapted to contain a row of sample tubes of uniform size. The sample holders may include a plurality of types, however, wherein each type is characterized by the size of the sample tube it is adapted to contain and the incremental spacing provided therebetween.

The various sample holder types have in common a registration surface on a first elongated side spaced a predetermined distance from the center line of the sample tubes. A horizontal groove extends the length of the second elongated side of each sample holder.

A first continuous conveyor means is provided on one side of the operating station for conveying the sample holders positioned thereon in a first longitudinal direction toward the operating station. Guide means adjacent one end of the first conveyor means are provided to halt the longitudinal motion of sample holders in the first longitudinal direction, and to define a first longitudinal stop position for each sample holder. The first longitudinal stop position is located adjacent the operating station.

Lateral drive means engage each sample holder in the first longitudinal stop position and move it laterally along the guide means into and then away from an operative position at the operating station. The lateral drive means include a continuous roller chain disposed generally about the periphery of the storage compartment. Means are provided for supporting and driving the chain, which has a path of travel alongside the first longitudinal stop position and past the operating station. A plurality of dogs are mounted to the chain for engaging and driving sample holders when the sample holders are in the first longitudinal stop position.

In accordance with another aspect of the invention, encoded label means are displayed on each sample holder for indicating the incremental spacing between the sample tubes carried in the sample holder. Also, detector means are mounted on the sample holder storage compartment ahead of the operating station for reading the encoded label means. The output signal of the detector means is indicative of the incremental spacing between the sample tubes carried in the sample holder. Control means are provided for receiving a signal from the detector means and causing the lateral drive means to move the sample holder in accordance with the signal. The lateral drive means, thereby, automatically position, in turn, each sample tube of the sample holder in an operative position at the operating station.

In accordance with further aspects of the invention, contact means are provided for engaging and stabilizing each sample holder while it is in the first longitudinal stop position. The contact means cause the sample holder to abut the guide means and resist any upward motion that may be imparted to the sample holder by the operating station when the sample holder is in an operative position.

DETAILED DESCRIPTION

Figure 1:
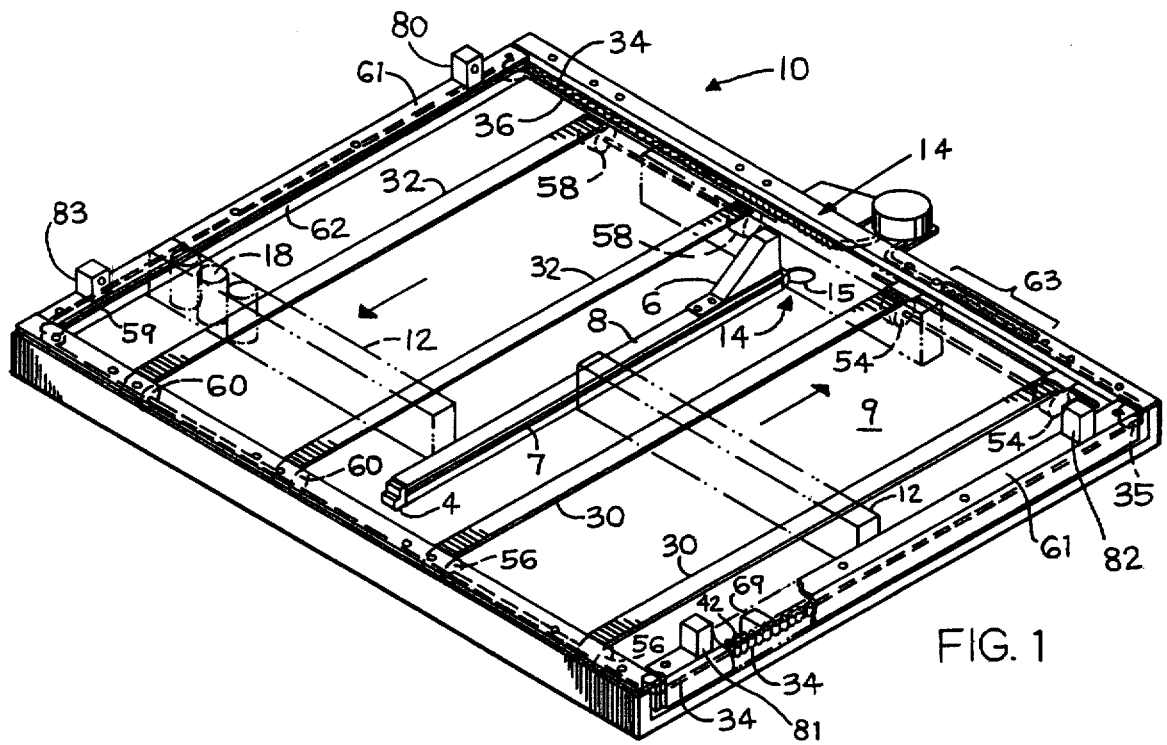
FIG. 1 is a perspective view of the transport apparatus of the invention.

In FIG. 1 there is shown a storage compartment and sample transport apparatus as employed in systems such as a radiation measuring analyzer. Reference numeral 10 designates the storage compartment which is generally rectangular and adapted for supporting a plurality of sample holders 12. The sample holders are circulated along a rectilinear path past an operating station 14.

In accordance with one important aspect of the present invention, the sample transport apparatus is designed to circulate along a rectilinear path any desired number of sample holders 12 from one up to a full load. To accomplish this, the sample transport apparatus includes a first and second parallel conveying means which engage and drive the sample holders in first and second opposite directions toward and away from the operating station 14.

The first conveying means includes a pair of conveyor belts 30 on which the sample holders 12 are supported for horizontal movement in the direction of the arrow toward the operating station 14. The second conveyor means includes a second pair of conveyor belts 32, generally parallel to belts 30, on which sample holders 12 are supported for horizontal movement in the opposite direction away from the operating station 14. The two conveyors 30 and 32 thus frictionally engage and drive sample holders 12 in opposite longitudinal directions in a horizontal plane.

Figure 6:
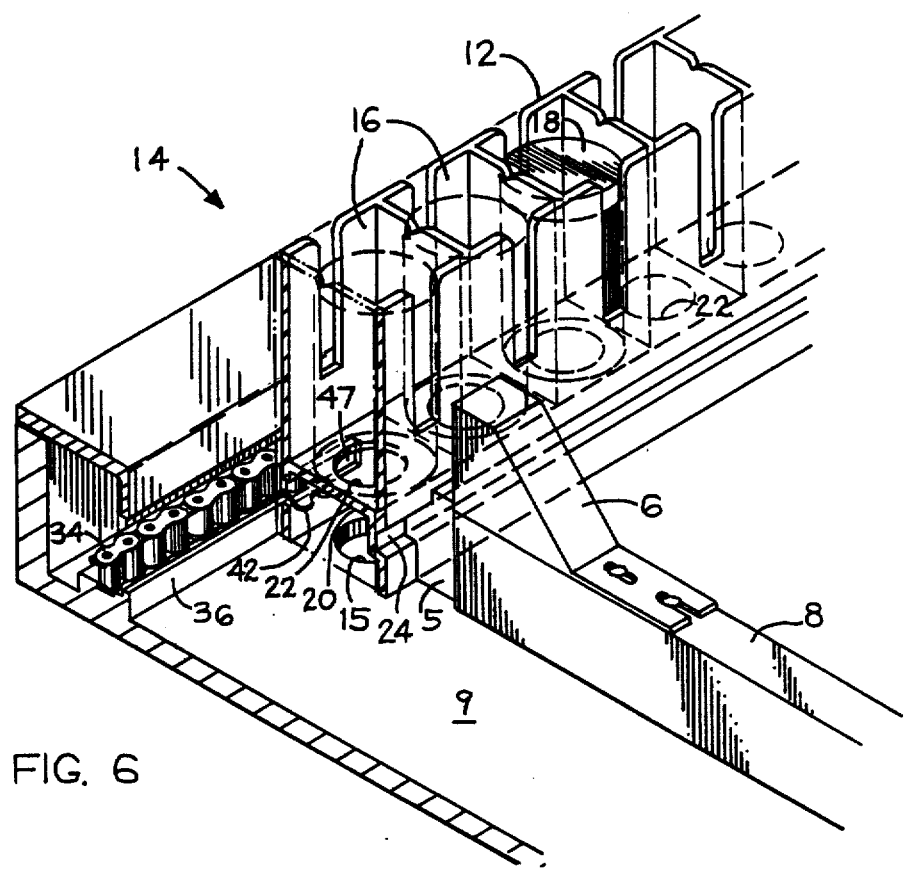
FIG. 6 is a fragmentary perspective view of a sample holder in an operating position with the apparatus of FIG. 1.

First and second guide means 36 (only one of which is shown and is best illustrated in FIGS. 1 and 6), are provided adjacent opposite ends of the first and second conveyor means for halting the motion of sample holders in the first and second directions, respectively, and to define first and second longitudinal stop positions for each sample holder. The first sample holders on the first and second conveyors therefore are driven until arriving at first and second longitudinal stop positions at the end of the respective conveyors.

After the first sample holder on the conveyor 30 arrives at the first longitudinal stop position, it is stepped laterally by lateral drive means between the conveyors 30 and 32 past the operating station 14. During such stepping motion, each sample tube 16 contained in sample holder 12 is positioned in turn at the operating station 14 for analysis. While this is taking place, a sample holder positioned on the second conveyor means will have reached the second longitudinal stop position and will be stepped laterally in synchronism with the movement of the first sample holder past the operating station.

At the end of such lateral movement, the sample holders occupy first and second lateral stop positions on the conveyors 32 and 30, respectively, which once again transport the sample holders in a longitudinal direction. Thus, rectilinear circulation of sample holders in a counterclockwise direction along and between the two conveyors continues during operation of the sample transport apparatus 10.

It should be noted that although rotation of sample holders along a counterclockwise path is the normal mode of operation for the apparatus described, the apparatus is fully capable of operation in the reverse direction for the purpose of repeating operation on one or more selected sample holders. Also, it should be noted that operation may be carried out with any number of sample holders 12 ranging from one to a full load. In this regard, a full load is the maximum number of sample holders that can be positioned on each conveyor 30 and 32 minus two large or three small type sample holders on each conveyor to allow for shifting of holders between conveyors.

By way of further description of the sample transport apparatus of sample storage compartment 10, the conveyor belts 30 of the first conveyor means are driven by a pair of motor driven pulleys 54 and pass around a pair of idler pulleys 56 at opposite ends thereof. Similarly, belts 32 of the second conveyor means are driven by motor driven pulleys 58 and pass around respective idler pulleys 60 at their opposite ends. A pair of bidirectional motors (not shown) are each connected to the driving pulleys 54 and 58, respectively, to power the first and second conveyor means independently of each other. In this arrangement, the belts slide over the top surface of the sample compartment base 9 and the belts 30 are driven in the first longitudinal direction while the belts 32 are driven in a second and opposite longitudinal direction.

In the center of the storage compartment base 9 is an elongated center divider 8, disposed longitudinally, and positioned between and generally parallel to the conveyors 30 and 32. The center divider includes a longitudinal slot 7 on one elongated side, and a sensor housing 6 mounted at the end adjacent the operating station 14. The sensor housing 6 contains photo-optical means (not shown in detail) for detecting the presence of a sample tube 18 in each of the compartments 16 of sample holder 12 when it is in an operative position at the operating station 14.

The perimeter of the sample holder storage compartment 10 is bounded by vertical sides having overhanging top members 61 which enclose a drive chain 34 thereunder. First and second guide means 36 (see FIG. 1 and FIGS. 6-8) are provided adjacent the first and second longitudinal stop positions, respectively. The first and second guide means 26 comprise a low ridge or shoulder which extends vertically from the storage compartment base 9. The first and second guide means 36 halt the motion of sample holders in the first and second directions, respectively, and provide a surface against which the sample holders are abutted while traveling in a lateral direction.

Located adjacent the outward sides of conveyors 30 and 32 are third and fourth guide means 62, respectively. Only one of these, the fourth guide means, is shown (FIG. 1). The third and fourth guide means comprise a vertical shoulder extending upward of storage compartment base 9. A guide slot 59 is defined by the space between the top of the fourth guide means 62 and the overhanging top member 61.

The third and fourth guide means 62 halt the lateral motion of sample holders 12 traveling between conveyors 30 and 32. By so doing, the third and fourth guide means define respective first and second lateral stop positions for each sample holder 12 when it is on conveyors 30 and 32.

Figure 2:
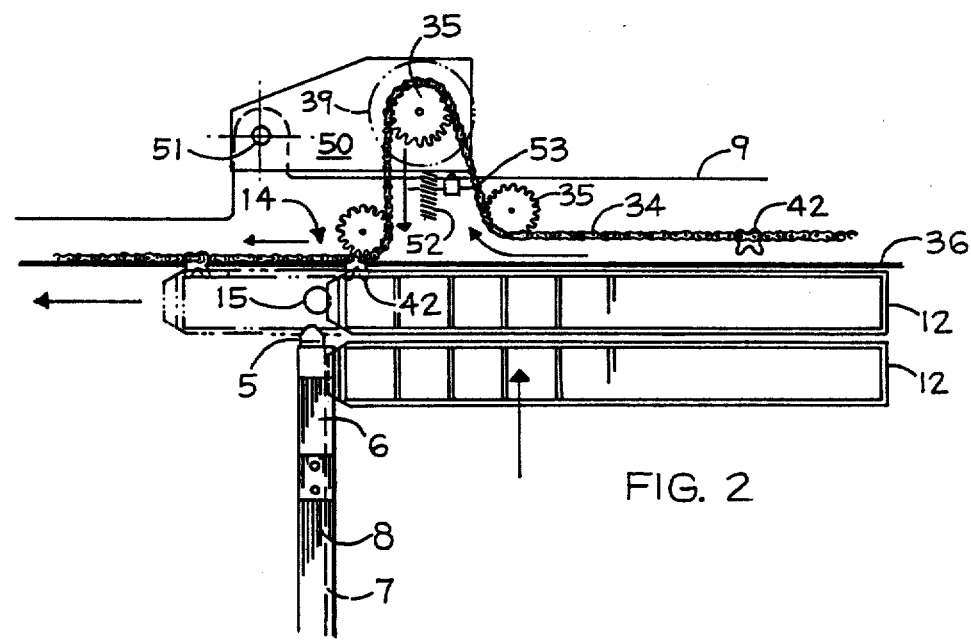
FIG. 2 is a fragmentary top view with a cover removed to show a portion of a chain drive included in the apparatus of FIG. 1.

Referring now also to FIG. 2, the lateral drive means which provides the stepping motion previously described will be explained in detail. The lateral drive means comprise a continuous roller drive chain 34 disposed generally about the periphery of the storage compartment base 9. The drive chain 34 is supported by a plurality of sprockets 35. One sprocket 35 is mounted at each point at which the chain changes direction and one sprocket 35 is mounted on stepper motor 39 which supplies the motive power to the drive chain 34. A plurality of dogs 42 are mounted on the chain at spaced intervals for engaging and driving sample holders 12 when the sample holders are in the first and second longitudinal stop positions.

In another important aspect of the invention, the hinged plate 50 upon which stepper motor 39 is mounted, is hinged to storage compartment base 9 through hinge pin 51. A spring 52 exerts an outward force on plate 50 and thereby maintains tension on drive chain 34. The position of hinged plate 50 is sensed by switch 53 mounted on storage compartment base 9 and connected to control means controlling the action of stepper motor 39. When the drive chain tension on either side of stepper motor 39 increases sufficiently to overcome the resisting force of spring 52, the continued rotation of the stepper motor causes the hinged plate 50 to pivot in the direction of the storage compartment base 9, thereby actuating switch 53. Switch 53 is connected to control means which include a microprocessor and which causes the stepper motor 39 to reverse its rotation for a specified time. By virtue of this arragement, jam-ups or stoppages in the lateral drive system such as might be caused by a mispositioned sample holder are sensed and automatically corrected.

Figure 3:
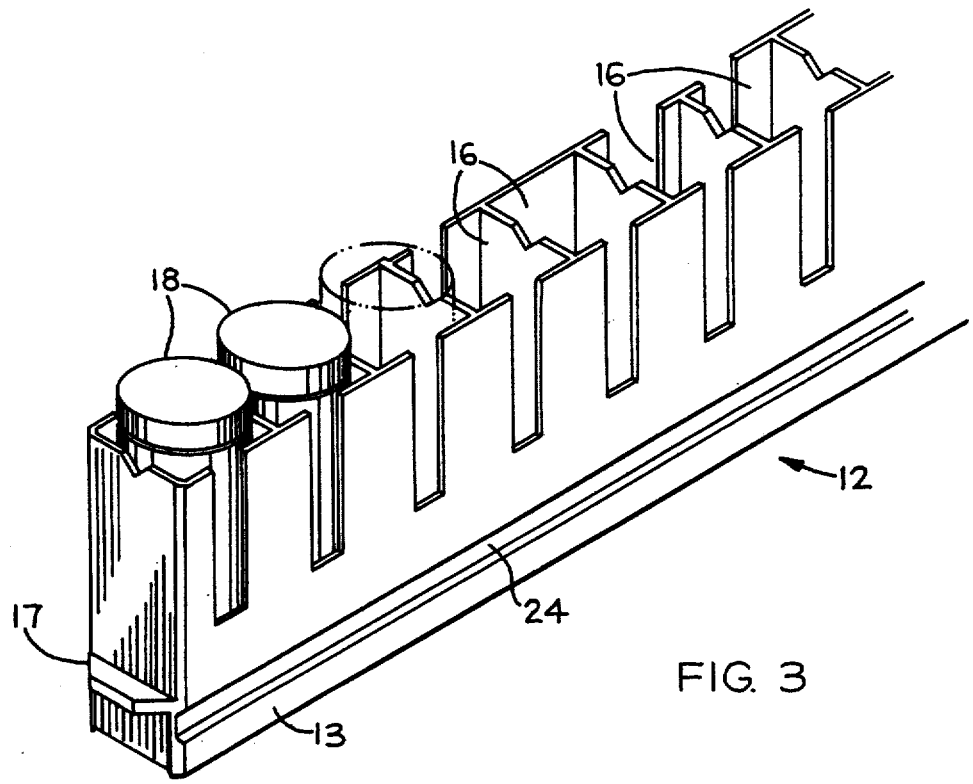
FIGS. 3 and 4 are partial perspective views of a sample holder employed in the practice of the invention.
Figure 4:
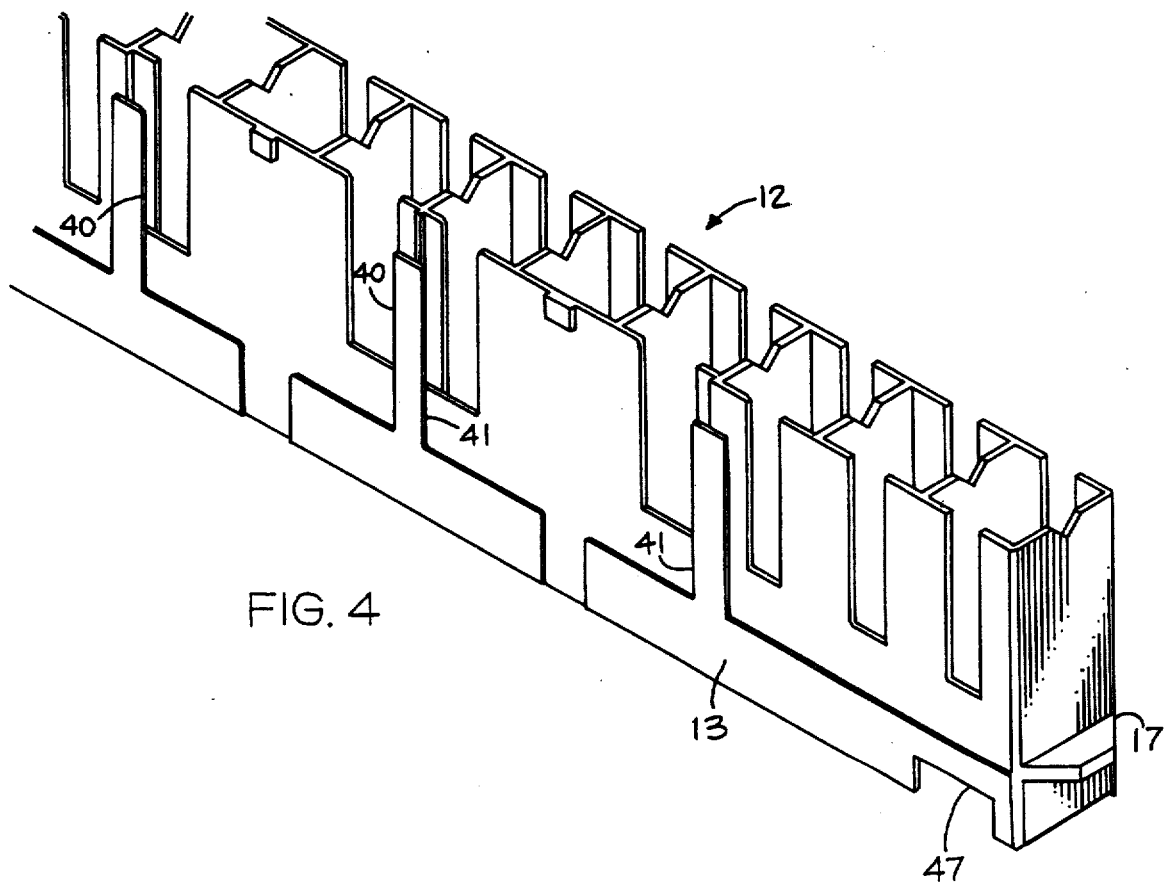
Figure 5:
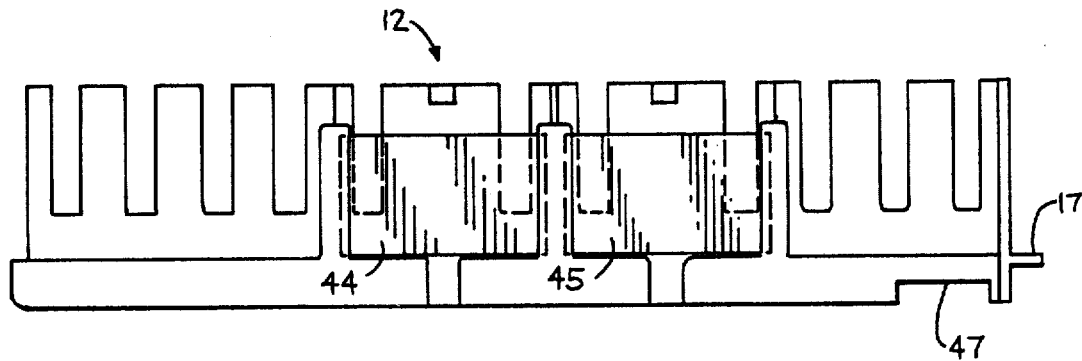
FIG. 5 is an elevation view of the sample holder of FIGS. 3 and 4.

Turning now to FIGS. 3–5 there is shown a suitable sample holder 12. Sample holder 12 has a generally rectangular base 13 supporting a row of tube compartments 16, each of which is adapted to receive and support a sample tube 18. A horizontal groove 24 is provided along one side of the sample holder base 13 and a tab 17 is provided at the left end of the sample holder 12 with respect to the side having horizontal groove 24 (FIG. 3).

When the sample holder 12 is being conveyed longitudinally to the first longitudinal stop position, tab 17 rides in longitudinal slot 7 in center divider 8 as shown in FIG. 1. Tab 17 in cooperation with longitudinal slot 7 serves to keep the sample holder 12 upright during the course of such travel. Similarly, when the sample holder 12 is being conveyed in the opposite direction (toward the second longitudinal stop position), tab 17 rides in the guide slot 59 formed by the fourth guide means 62.

Referring now specifically to FIGS. 4 and 5, attention is directed to the opposite side of sample holder 12 wherein there are provided two label holders 40 and 41 for holding label means 44 and 45. Label means 44 and 45 contain indicia which in conjunction with label detector means 63 (FIG. 1) convey information to the control means for controlling the operation of the sample transport apparatus. This aspect of the invention will be further described herein elsewhere. Attention is also directed to the drive slot 47 of sample holder 12 which is adapted for receiving and engaging a dog 42 of drive chain 34.

When a sample holder 12 arrives in the first longitudinal stop position, its longitudinal motion is halted upon abutting the guide means 36. The sample holder remains in this position for a few seconds, until one of the dogs 42 of lateral drive chain 34 reaches the sample holder and engages its drive slot 47. During this brief waiting time, the belts (of the first conveyor means 30) upon which the sample holder is positioned, continue running in slipping engagement with the sample holder, which serves to keep the sample holder in abutting contact with the guide means 36. Upon engaging the sample holder 12, the lateral drive means moves it laterally, so that the first compartment 16 is at the operating stating 14.

Referring now to FIG. 6 and more particularly to the sample holder 12 shown therein, it will be seen that sample tube 18 is disposed in compartment 16 and rests on the floor 20 thereof. The floor 20 of each compartment 16 includes a circular opening 22 which is of smaller diameter than the sample tube 18. While the sample holder 12 is at the operating station 13, the lateral drive means positions each compartment 16 of sample holder 12 in an operating position. While in such position, circular opening 22 is in general alignment with the aperture 15 in the storage compartment base 9.

as previously discussed, the apparatus of the invention is suited for use in analytical instrumentation wherein it is required that each sample tube be, in turn, extracted from the sample holder, analyzed in an analytical chamber, and then returned to the sample holder. To accomplish this, an elevator system having an upwardly moving elevator rod is typically employed and well known in the art.

As employed by the apparatus of the invention, an elevator rod (not shown) extends upwardly through aperture 15 of storage compartment base 9. The elevator rod passes through circular opening 22 of sample holder 12 and lifts sample tube 18 out of its compartment 16 and into an analytical chamber (not shown). When the analytical operation is completed, the elevator rod lowers to return the sample tube 18 to its respective compartment 16, whereupon the lateral drive means positions the next compartment in the operating position and the sequence is repeated.

Figures 7, 8:
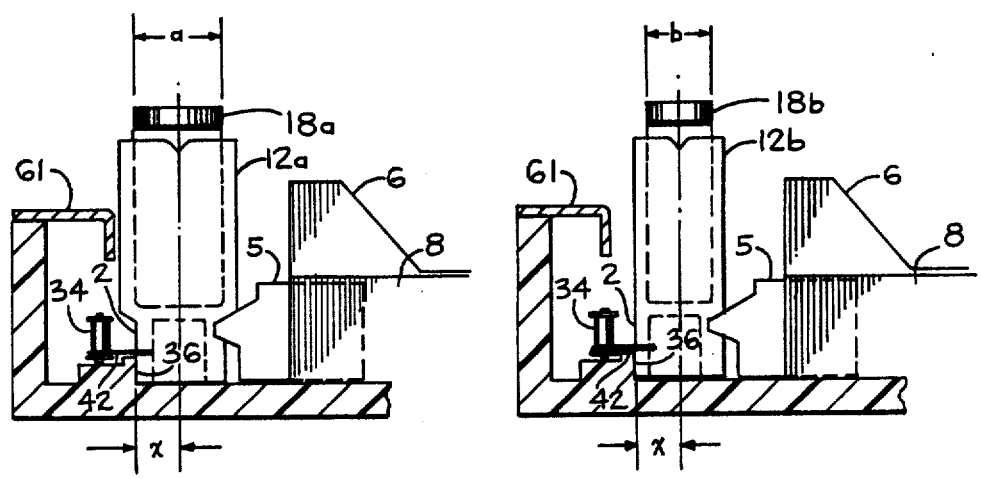
FIGS. 7 and 8 are end views of two types of sample holders, each adapted to hold sample tubes of a given size.

Referring now to FIGS. 6–8 the sample holder 12 is shown at operating station 14. The center divider 8 is disposed generally in line with operating station 14, and at the end adjacent thereto is provided a first contact member 5 for engaging and stabilizing sample holders 12 in the first longitudinal stop position. The first contact member 5 is configured for engaging the horizontal groove 24 of the sample holder 12 in sliding engagement therewith. This arrangement enables the sample holder to be driven laterally, while engaged with the first contact member 5. The first contact member 5 is spring loaded by spring means (not shown) which enables it to impart a force to the sample holder 12, causing it to closely abut the guide means 36 and maintain engagement with dog 42 of the lateral drive means. In addition to this, the first contact member 5 functions as a "hold down" to prevent the sample holder 12 from lifting if, through minor misalignment, it is contacted by the upwardly traveling elevator of the operating station 14.

In the preferred form, the horizontal groove 24 of sample holder 12 and the contact member 5 have mating "V" configurations. However, other configurations. such as a rectangular tongue-in-groove configuration may also be used. The "hold down" capability of the first contact member 5 is not required at the second longitudinal stop position, as there is no elevator at this location. Accordingly, the second contact member 4 located adjacent this location is configured for simply bearing against the sample holder base 13 to ensure that the sample holder remains engaged with the dog 42 of the lateral drive means.

Turning now to FIGS. 7 and 8, another important aspect of the invention will be described. As shown in the partial end views in which extraneous detail is omitted, sample holders 12a and 12b contain sample tubes 18a and 18b, respectively. The sample holders are each shown engaged with first contact member 5, and in abutting contact with guide means 36. For the purpose of discussion, the portion of the sample holder abutting guide means 36 is designated as reference surface 2.

Now, by noting that diameter "a" of sample tube 18a is markedly larger than diameter "b" of sample tube 18b, it will be readily apparent that sample holders 12a and 12b represent distinguishable types, wherein each type is adapted to contain a particular size sample tube. Since it is desirable for the operation of the transport apparatus that the overall length of sample holders remain constant, the number of sample tubes and the incremental spacing between the tubes contained in any given sample holder type is therefore a function of the tube diameter. Similarly, the width of various sample holder types must also vary according to the tube diameter.

A number of provisions incorporated by the invention enables the transport apparatus to accommodate various sample holder types in any order or mixtures thereof, automatically. First, it will be seen that although the upper portion of the sample holder type designated 12a is larger than that of 12b, the base portions of both types are identical. More specifically, the dimension marked "X" which is the distance between the tube center line and reference surface 2 is the same for both holder types. Thus, in the longitudinal direction, the alignment of the respective holder types is assured.

As previously stated, the lateral positioning of sample holders at operating station 14 is carried out by the lateral drive means. The operation of the lateral drive means, in turn, is governed by control means which include a microprocessor and a plurality of detector means which feed information to the microprocessor. More specifically, each sample holder is provided with means for carrying label means 44 and 45, respectively, as shown by FIGS. 4 and 5. The label means are suitably encoded, as by means of alternating black and white indicia appearing thereon, to display information pertaining to the sample holder type, identity, contents and selected program options. The label means 44 and 45 are scanned by label detector means 63 (FIG. 1) which are mounted proximate guide means 36 at the first longitudinal stop position.

Label detector means 63 comprises an array of photooptical detectors suitable for reading binary coded indicia and the like. However, if desired, other label means and other methods of encoding and detecting same may be employed. For example, the labeling means could be magnetically encoded and read by suitable magnetically responsive detectors.

Referring now to the block diagram of FIG. 9, the major functions of the control means with regard to the operation of the sample transport apparatus will be described. When a sample holder 12 arrives at the first longitudinal stop position, label means 44 and 45 are "read" by label detector means 63, which provide signals to the microprocessor 66 portion of the control means. Included in these signals is information as to the sample holder type. This information enables the control means to cause the stepper motor 39 to advance the correct number of steps to position the first and suceeding compartments 16 of the sample holder 12 in operating position at the operating station 14.

A sensor may be optionally employed in the sensor housing 6 to detect missing sample tubes in a partially filled holder in order that the operating sequence applied to the vacant stations be omitted. In addition, the information transmitted by the label detector means 63 includes the identity of the specific sample holder and enables the control means to implement specific options in the operatig or analytical process.

Other inputs to the microprocessor 66 include a signal from switch 53 which detects jam-ups in the transfer apparatus by an increase in chain tension. Upon receiving such indication, the control means causes the first and second longitudinal drive motors 67 and 68, respectively, to alternately reverse directions in conjunction with reversing the stepper motor 39, to correct the jam-up.

Another input to the microprocessor 66 is from the dog sensors 69 which will be discussed, initially, in general terms. The precision registration of sample holders at the operating station is the result of the microprocessor causing the stepper motor to step the exact number of steps required for each movement of the sample holder. It is, therefore, necessary for the microprocessor to "know" the step-distance between the operating station and the next approaching dog. If the transport apparatus traveled only in one direction, it would be a simple matter to establish this distance as a fixed mechanical relationship. Bi-directional travel, however, introduces backlash error, making it necessary to provide means for establishing the step-location of a dog as it approaches the operating station.

As the drive chain is of fixed length, and the seven dogs mounted thereon are spaced equally apart, the position of all dogs can be established upon fixing the position of one. Accordingly, first and second dog sensors 69, one of which is shown by FIG. 1, are located one on each side of the operating station 14 at a point which may be substantially removed therefrom. The first dog sensor 69 is used for detecting the passage of dogs 42 traveling in the forward direction, and the second dog sensor (not shown) is used for detecting the passage of dogs traveling in the reverse direction. Thus, by detecting the presence of a dog 42 at, say, the first dog sensor 69, which is a known step-distance from the operating station, the position of any dog intermediate the sensor and the station is determinable, since the distance between dogs is also a known constant.

When the sample holder 12 arrives at the operating station 14, the first compartment of the sample holder 12 is positioned in the operating position. Upon completion of the operating cycle, the microprocessor 66 causes the stepper motor 39 to step an additional number of steps, in accordance with the sample holder type, to position the next compartment 16 in operating position. The process is repeated, so that each compartment 16 is sequentially positioned at the operating station. As previously discussed, the operating cycle may be skipped for compartments not containing a sample tube 18, by use of optional tube detector 6. When the sample holder 12 has completed its operating cycle at the operating station 14, the lateral drive means transports it to the first lateral stop position, and the next following sample holder is moved into operating position.

Referring again to FIG. 1, four corner sensors 80–83 are shown. The first pair, corner sensors 80 and 81, are positioned at diagonally opposed locations at the periphery of the sample holder storage compartment, adjacent the first and second longitudinal stop positions, respectively. The second pair of corner sensors 82 and 83 are similarly deployed at opposite diagonal locations on the perimeter of the sample holder storage compartment. The first pair of sensors 80 and 81 are employed during operation of the transport apparatus in the normal (counterclockwise) direction, and the second pair of sensors 82 and 83 are used during operation in the reverse (clockwise) direction.

Figure 9:
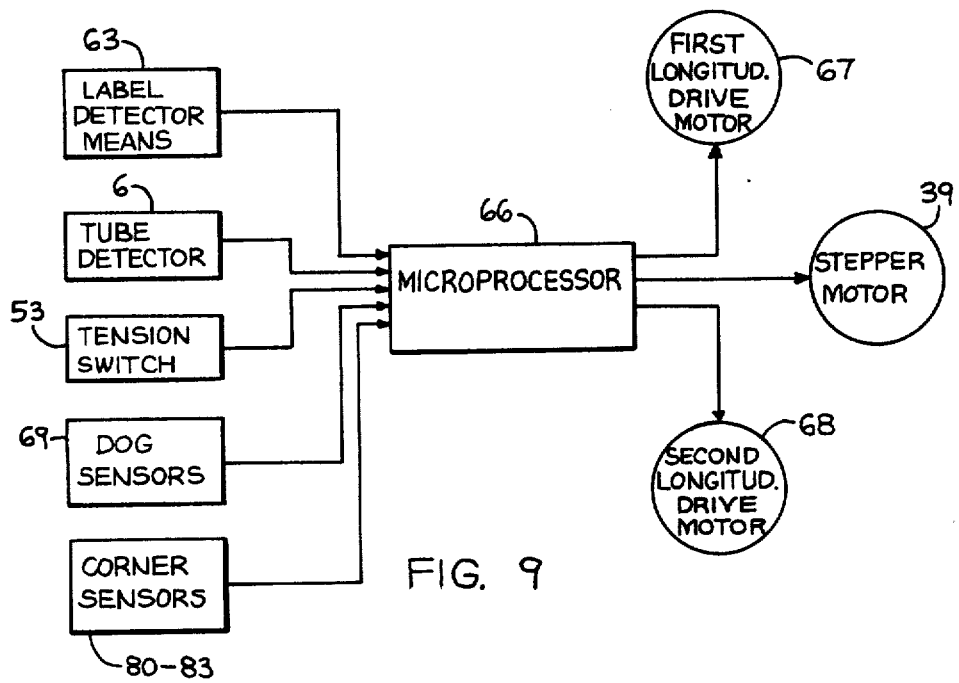
FIG. 9 is a simplified block diagram of a control means for the transport apparatus of FIG. 1.

The corner sensors 80–83 cooperate with the microprocessor control means 66 shown in FIG. 9 to regulate the quantity of sample holders occupying the first and second conveyor means. When operation is carried out with sample holders of differing types (i.e. widths), it becomes necessary to prevent filling up the space on either conveyor in order to provide space for the next arriving sample holder. Although during operation the sample holders are exchanged between the first and second conveyor means on a one-for-one basis, and imbalance can develop between the respective conveyor means. The imbalance is not in terms of the quantity of sample holders occupying each conveyor (this remains constant), but rather, in terms of the space which is occupied by the sample holders.

To illustrate by means of an extreme example, if one conveyor means were fully loaded with narrow sample holders and the other conveyor means fully loaded with wide sample holders, it will be readily seen that in exchanging narrow holders for wide ones the first conveyor means would soon develop a shortage of space in which to receive the wide sample holders. It would of course be possible to simply limit the number of narrow sample holders used, but this would reduce the utility of the apparatus. Accordingly, provision is made of the apparatus to automatically regulate the distribution of sample holders on the respective conveyor means in accordance with the space available thereon.

To further illustrate the operation of corner sensors 80 and 81, consider the condition whereby a first sample holder 12 following operation at the operating station 14 is transported laterally to the first lateral stop position to be engaged and transported longitudinally by the second conveyor means 32. If the corner sensor 80 senses that the space on conveyor means 32 adjacent the first lateral stop position is not vacant (this space being at least equivalent to the width of the widest sample holder in use), the microprocessor control means 66 will conclude that conveyor means 32 is overloaded. The control means 66 will therefore cause the first conveyor means to stop and to reverse momentarily. This action prevents the delivery of another sample holder from the first conveyor means 30 to the second conveyor 32. The sample holder 12 whic was formerly at the first longitudinal stop position, to be next engaged by the lateral drive means, is backed away from the stop position by the momentary reversal of the conveyor, thereby precluding its being engaged by the lateral drive means. The second conveyor means, however, continues to be driven in the direction away from the operating station 14. This enables a sample holder adjacent the second longitudinal stop position to be engaged by the lateral drive means and transported from the second conveyor means 32 to the first conveyor means 30. This action eliminates the overload condition on the second conveyor means 32, and enables normal operation to be resumed.

The automatic regulating process that has been described may be repeated as often as required. If an overload condition develops on the first conveyor means 30, corner sensor 81 detects the presence of a sample holder 12 in the space adjacent the second lateral stop position on conveyor means 30. In similar fashion, the microprocessor 66 will cause the second conveyor means 32 to stop and momentarily reverse to stop feeding sample holders 12 to the overloaded conveyor means 30. The overload is relieved therefore in the manner previously described.

Corner sensors 82 and 83 serve in the same manner as corner sensors 80 and 81 when operation of the transport apparatus is carried out in the reverse direction.

While in accordance with the patent statutes there has been described what at present is considered to be the preferred embodiment of the invention, it will be understood by those skilled in the art that various changes and modifications may be made therein without departing from the invention and it is, therefore, the aim of the appended claims to cover all such changes and modifications as fall within the true spirit and scope of the invention.

What is claimed is:

1. In a transport system for circulating sample holders of mixed widths along a rectilinear path, past an operating station in a sample holder storage compartment having first and second parallel conveyors disposed one on each side of said operating station for conveying sample holders positioned thereon in first and second opposite longitudinal directions toward and away from said operating station;
   first and second bidirectional drive means for driving said first and second conveyors respectively;
   guide means adjacent each end of said first and second conveyors for halting the motion of sample holders in said first and second longitudinal directions, respectively, and to define first and second longitudinal stop positions for each sample holder;
   said first longitudinal stop position and situated adjacent said operating station;
   lateral drive means for engaging each sample holder in said first and second longitudinal stop positions and for moving said sample holders laterally along said guide means beteen said first and second conveyor means to a first or second lateral stop position, said lateral drive means moving said sample holder into and then away from an operating position at said operating station when said sample holder reaches said first longitudinal stop position;
   said transport system including:
      regulating means for automatically regulating the quantity of sample holders occupying said first and second conveyor means in accordance with space available thereon;

said regulating means including first and second sensor means operative when said transport system is operated in a counterclockwise direction, for sensing when one of said first or second conveyors is fully occupied by sample holders positioned thereon; and control means responsive to said first and second sensor means for stopping and momentarily reversing the direction of one of said first or second conveyors when the other conveyor is filled with sample holders so as to prevent the transfer of additional sample holders by said lateral drive means to said conveyor.

2. The transport systsem defined by claim 1 wherein said first sensor means being arranged to sense the presence of a sample holder on said second conveyor at a distance from said first lateral stop position equal to twice the width of the widest sample holder in use.

3. The transport system defined by claim 1 wherein said second sensor means being arranged to sense the presence of a sample holder on said first conveyor at a distance from said second lateral stop position equal to twice the width of the widest sample holder used in the transport system.

4. A transport system for circulating sample holders along a rectilinear path, past an operating station in a sample holder storage compartment having first and second parallel conveyors on opposite sides of said operating station for conveying sample holders positioned thereon in first and second opposite longitudinal directions toward and away from said operating station;

first and second bidirectional drive means for driving said first and second conveyors respectively.

guide means adjacent each end of said first and second conveyors for halting the motion of sample holders in said first and second longitudinal directions respectively, and to define first and second longitudinal stop positions for each sample holder;

said first longitudinal stop position situated adjacent said operating station;

lateral drive means for engaging each sample holder in said first and second longitudinal stop positions and for moving said sample holders laterally along said guide means between said first and second conveyors to a first or second lateral stop position, said lateral drive means moving said sample holder into and then away from an operating position at said operating station when said sample holder reaches said first longitudinal stop position;

said transport system including:

regulating means for automatically regulating the quantity of sample holders occupying said first and second conveyors in accordance with space available thereon;

said regulating means including third and fourth sensor means operative when said transport system is operated in a clockwise direction for sensing when one of said first or second conveyors is fully occupied by sample holders positioned thereon;

control means responsive to said third and fourth sensor means for stopping and momentarily reversing the direction of one of said first or second conveyors when the other conveyor is filled with sample holders so as to prevent the transfer of additional sample holders by said lateral drive means to said conveyor.

5. The transport system definedby claim 4 wherein said third sensor means being arranged to sense the presence of a sample holder on said first conveyor at a distance from said first lateral stop position equal to twice the width of the widest sample holder in use.

6. The transport system defined by claim 4 wherein said fourth sensor means being arranged to sense the presence of a sample holder on said second conveyor at a distance from said second lateral stop position equal to twice the width of the widest sample holder used in the transport system.

* * * * *